(12) United States Patent
Jenkins, Jr. et al.

(10) Patent No.: US 7,192,544 B2
(45) Date of Patent: Mar. 20, 2007

(54) EARPLUG WITH MOLDED-IN STIFFENER

(75) Inventors: John Allen Jenkins, Jr., San Diego, CA (US); Jim Tiemens, Laguna Niguel, CA (US)

(73) Assignee: Howard Leight Industries, LLC, San Diego, CA (US)

( * ) Notice: Subject to any disclaimer, the term of this patent is extended or adjusted under 35 U.S.C. 154(b) by 0 days.

(21) Appl. No.: 10/937,211

(22) Filed: Sep. 9, 2004

(65) Prior Publication Data

US 2005/0056289 A1 Mar. 17, 2005

Related U.S. Application Data

(60) Provisional application No. 60/502,789, filed on Sep. 12, 2003.

(51) Int. Cl.
*B29C 67/00* (2006.01)
(52) U.S. Cl. ..................... 264/46.4; 264/278
(58) Field of Classification Search ............... 128/864, 128/866, 867; 181/129, 130, 134, 135; 264/278, 264/46.7, 46.4, 46.3
See application file for complete search history.

(56) References Cited

U.S. PATENT DOCUMENTS

| | | | |
|---|---|---|---|
| 2,538,339 A | 1/1951 | Thomas | |
| 2,888,921 A | 6/1959 | Nielson et al. | |
| 3,736,929 A * | 6/1973 | Mills | 128/864 |
| 3,800,791 A | 4/1974 | Visor | |
| 3,881,570 A | 5/1975 | Lewis | |
| 4,053,051 A | 10/1977 | Brinkhoff | |
| 4,434,794 A | 3/1984 | Leight | |
| 4,819,624 A * | 4/1989 | Leight et al. | 128/866 |
| 5,044,463 A * | 9/1991 | Carr | 181/135 |
| 5,080,110 A | 1/1992 | Weldon et al. | |
| 5,153,387 A | 10/1992 | Zwislocki et al. | |
| 5,188,123 A | 2/1993 | Gardner, Jr. | |
| 5,573,015 A | 11/1996 | Williams | |
| 6,006,857 A | 12/1999 | Leight et al. | |
| D423,664 S | 4/2000 | Falco | |
| 6,138,790 A | 10/2000 | Leight | |
| 6,148,821 A | 11/2000 | Falco | |
| 6,264,870 B1 | 7/2001 | Hakansson | |
| 6,568,394 B2 | 5/2003 | Falco | |
| 6,659,103 B2 | 12/2003 | Tiemens | |
| 6,695,093 B1 | 2/2004 | Falco | |
| 2002/0124851 A1 | 9/2002 | Knauer et al. | |
| 2003/0029458 A1 | 2/2003 | Tiemens | |

* cited by examiner

*Primary Examiner*—Patricia Bianco
*Assistant Examiner*—Camtu Nguyen
(74) *Attorney, Agent, or Firm*—Leon D. Rosen

(57) ABSTRACT

Earplugs with soft foam bodies and with stiffeners in the bodies, are molded by suspending the stiffener in the body mold cavity using a pin (60) that extends into a passage (56) at the rear of the body. Each stiffener is tapered in diameter, with a rear end (34) of greatest diameter.

6 Claims, 4 Drawing Sheets

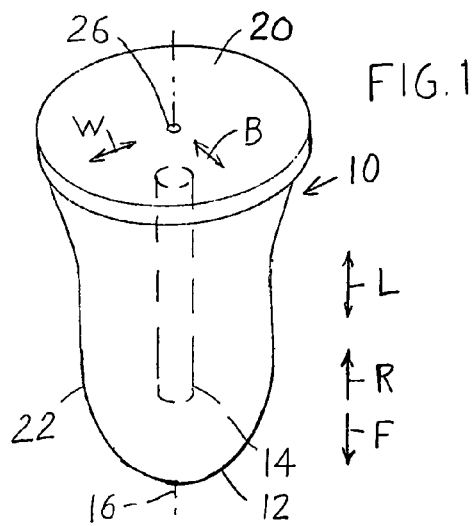
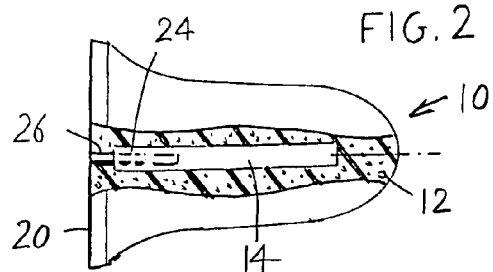
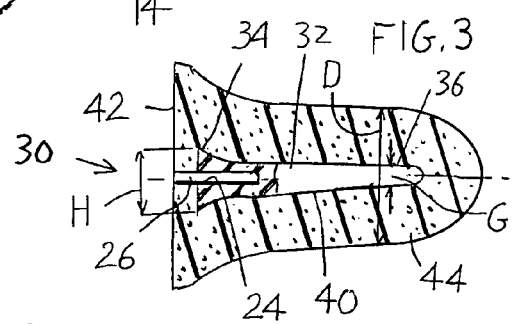
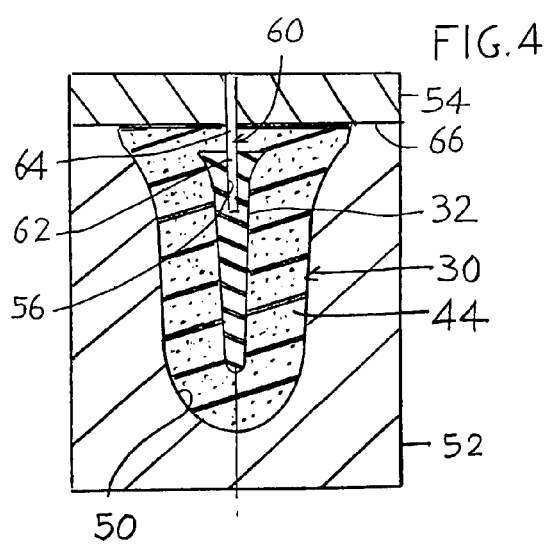
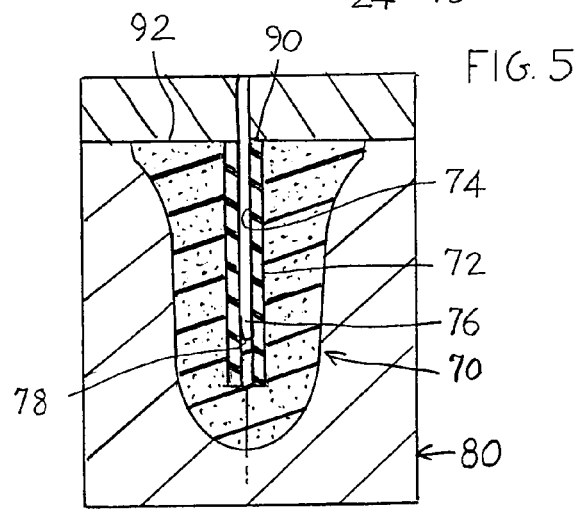
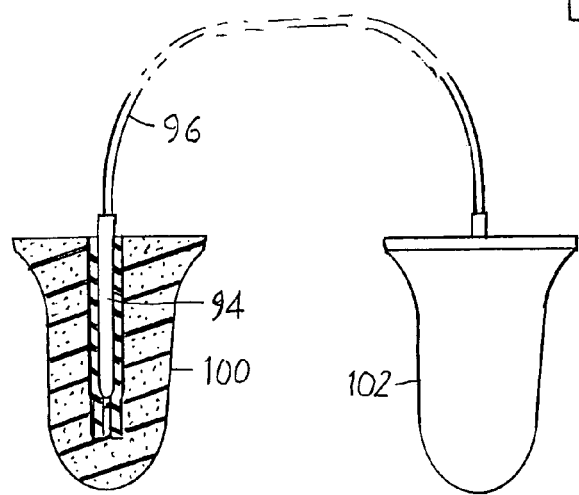

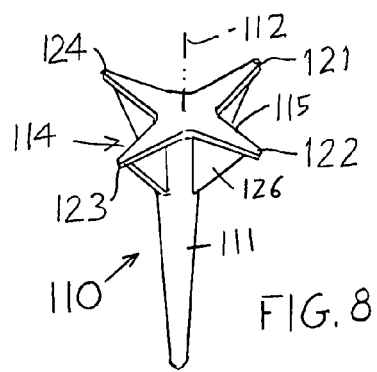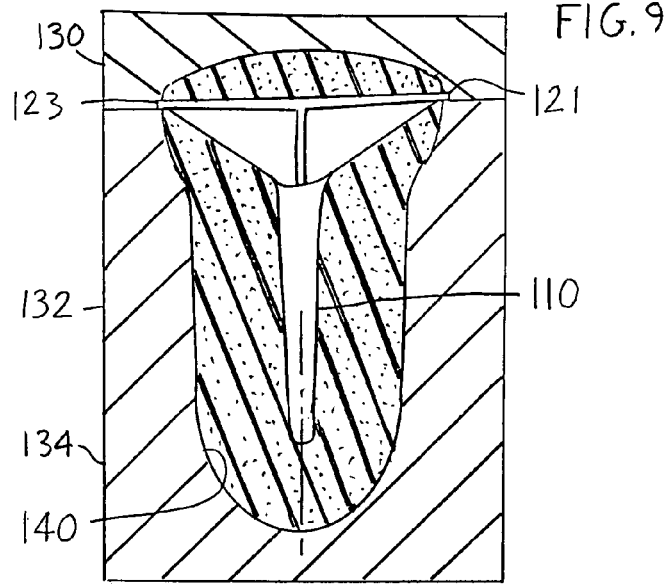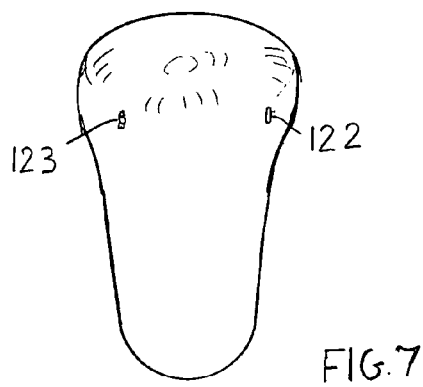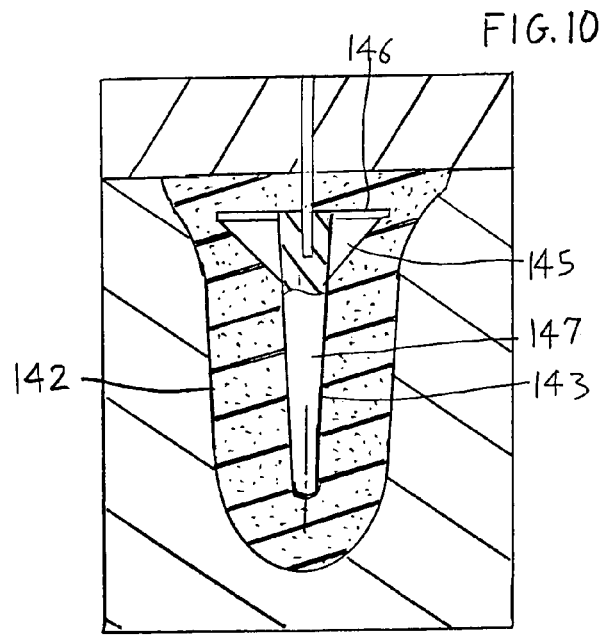

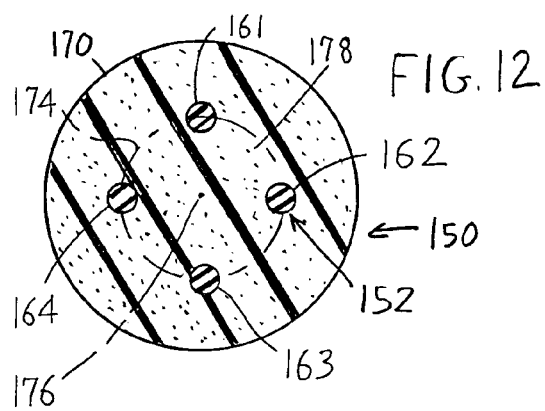
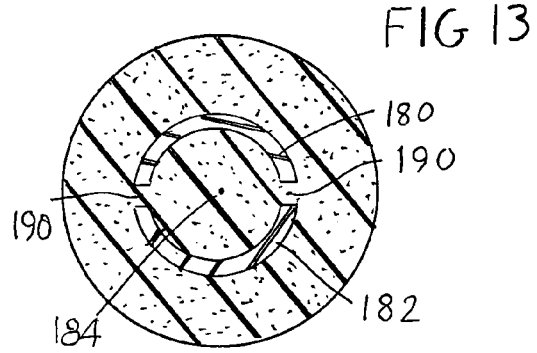
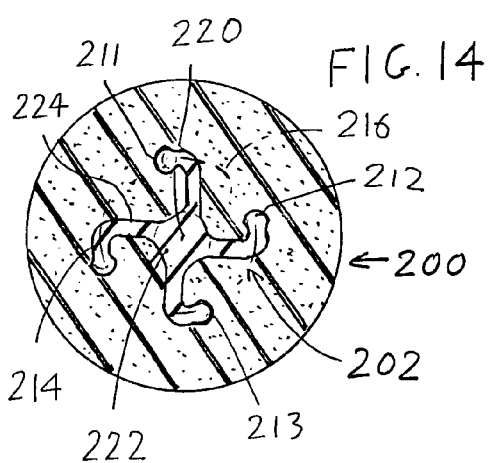
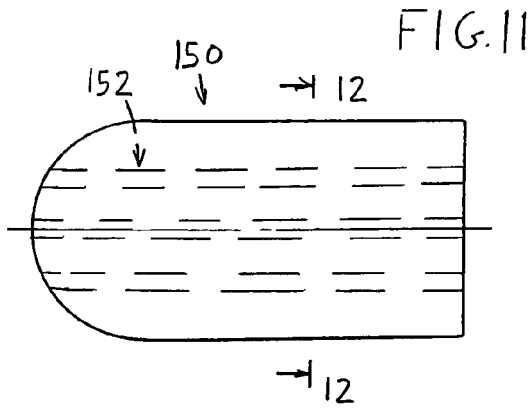
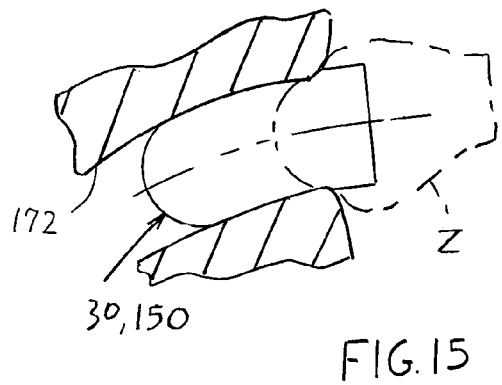

US 7,192,544 B2

EARPLUG WITH MOLDED-IN STIFFENER

CROSS-REFERENCE

Applicant claims priority from U.S. provisional patent application Ser. No. 60/502,789 filed Sep. 12, 2003.

BACKGROUND OF THE INVENTION

Earplugs formed solely of soft resilient foam material are difficult to insert into the ear canal. When the front end of the earplug lies against the entrance to the ear canal and the rear end of the earplug is pushed, the foam earplug collapses. During such collapse, as shown at Z in FIG. 15, the front end of the earplug enlarges in diameter and does not move into the ear canal. It has been found that a core of stiffer material, as in the form of a rod, can be placed in a soft resilient foam body to help insert the foam body into the ear canal. U.S. Pat. No. 5,573,015 by Williams shows a foam body molded around a stiffer core by extrusion.

Although an earplug with a stiffener that is exposed is acceptable to many people, an earplug with stiffener that is almost completely covered by the soft foam material of the body is often more acceptable, at first. The largely concealed stiffener does not remind a person that stiff material is to be inserted into his/her ear canal and raise fears (unfounded) of discomfort by the presence of stiff material. Thus, an earplug with a largely concealed stiffener would be of value. A method for forming such earplug with a largely concealed stiffener also would be of value.

Although a rod-shaped elastomeric stiffener helps in earplug insertion, it makes the earplug stiffer against bending. Many people have ear canals that are curved, so an earplug inserted into one of the ears must bend to follow the curvature of the ear canal. The stiffener resists bending, causing forces on the sides of the person's ear canal and consequent possible discomfort to the person. An earplug with a stiffener to help insertion, wherein the stiffener was sufficiently stiff against column collapse but was easily bent by the walls of the ear canal to avoid discomfort, would be of value.

Methods for establishing a stiffer of any desired shape in a mold cavity, at low cost, also is desirable.

SUMMARY OF THE INVENTION

In accordance with one embodiment of the invention, applicant provides an earplug with a soft earplug body, a stiffener extending within much of the length of the body, and an earplug manufacturing method therefor, wherein the stiffener is axially stiff but allows the body to easily bend. In one manufacturing method for an earplug that is molded in a two piece mold, the stiffener has a hole, or passage, in its rear end. A top part of the mold has a pin that is inserted into the hole in a slight press fit to hold the stiffener in the mold cavity. The stiffener may be held with a space left between the rear of the earplug and the mold top part, to conceal the stiffener in the final earplug. Foamable material is placed in the mold cavity and the mold is closed, with the stiffener held by the pin. When the foam material sets, the earplug is removed, with foam lying all around the stiffener, except for a hole at the rear of the earplug.

The pin on the upper mold part, that extends into a passage in the stiffener, can extend into a passage that is meant to hold an end of a cord of a type that holds two earplugs together. The unfilled passage part left in the final earplug can more easily receive a cord end.

A more bendable earplug is obtained by using a tapered stiffener, with its rear end wide and its front end narrow. A stiffener may include a plurality of stiffeners or stiffener portions that lie on a circle (as seen in a sectional view of the earplug) and with spaces between them.

An earplug body can be molded in a cavity, with a mandrel extending along the axis to leave a stiffener inner cavity. When the mandrel is removed, an elastomeric stiffener material is poured into the inner cavity and allowed to solidify.

The novel features of the invention are set forth with particularity in the appended claims. The invention will be best understood from the following description when read in conjunction with the accompanying drawings.

BRIEF DESCRIPTION OF THE DRAWINGS

FIG. 1 is a rear and side isometric view of an earplug of one embodiment of the invention.

FIG. 2 is a partially sectional side view of the earplug of FIG. 1.

FIG. 3 is a sectional view of the earplug of FIG. 2, but with a modified stiffener.

FIG. 4 is a sectional view of a mold in which the earplug of FIG. 3 is being molded.

FIG. 5 is a sectional view of another mold in which an earplug of the type illustrated in FIG. 6 is being molded.

FIG. 6 is a partially sectional view of a pair of earplugs, each of the type shown in FIG. 5, and with a cord with opposite ends anchored in the earplugs.

FIG. 7 is an isometric view of an earplug with another form of stiffener.

FIG. 8 is an isometric view of a stiffener of the earplug of FIG. 7, which has a rear portion of enlarged width.

FIG. 9 is a sectional view of a mold, in which an earplug with a stiffener of the type shown in FIG. 8 is being molded.

FIG. 10 is a sectional view of an earplug in a mold, with a stiffener of another embodiment of the invention.

FIG. 11 is a side view of an earplug with a plurality of stiffeners or stiffener portions spaced about a circle.

FIG. 12 is a sectional view taken on line 12-12 of FIG. 11.

FIG. 13 is a sectional view of an earplug similar to that of FIG. 11, but with stiffeners or stiffener portions of a different construction.

FIG. 14 is a sectional view of an earplug similar to that of FIG. 11, but with stiffeners or stiffener portions of a different construction.

FIG. 15 is a sectional view of an earplug fully inserted into an ear canal that is curved, and also showing how a purely foam earplug would collapse.

DESCRIPTION OF THE PREFERRED EMBODIMENTS

Figure 16:
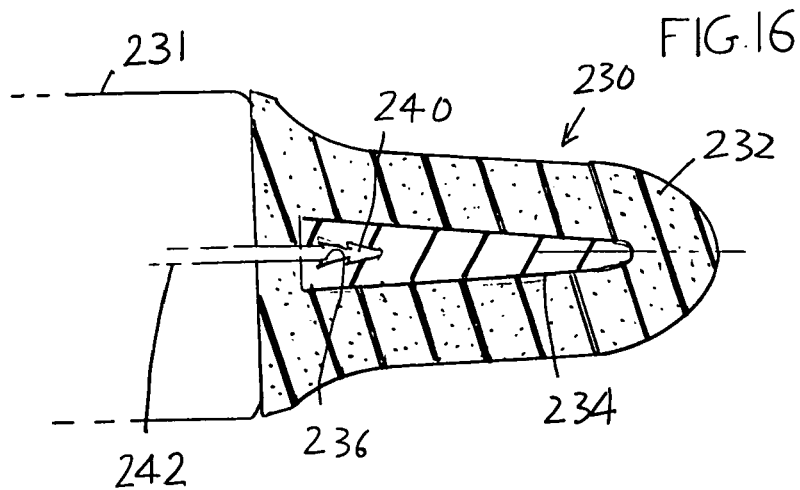
FIG. 16 is a sectional view of an earplug mounted at an end of a head band.

FIGS. 1 and 2 illustrate an earplug 10 which has a body 12 of soft resilient foam and a stiffener 14 that is of stiffer material than that of the body and that extends part of the distance along the earplug axis 16. The stiffener is constructed of elastomeric material, which is resilient material having a Young's modulus of elasticity of no more than 50,000 psi. It is possible to construct the body of a slow recovery foam which is resilient but with the recovery after deflection being delayed. The stiffener is useful during earplug insertion into a person's ear canal, by the person pushing against the rear end 20 of the earplug to force the front end portion 22 of the earplug, which seals the ear canal, to enter the ear canal. The earplug is elongated in front F and rear R directions, also indicated by arrows L. The stiffener prevents the body front end portion 22 from collapsing during insertion and thereby increasing in diameter. The stiffener 14 shown in FIG. 2 is in the form of a rod with an elongated narrow hole 24 in its rear end. The body has a narrow hole 26 extending to the body rear end 20. Except for the narrow body hole 26, there is no indication that there is a stiffener in the earplug. The hole 26 is long and narrow enough, with a length in direction L more than the width in directions W and more than the breadth in directions B (both perpendicular to the length L) so the stiffener cannot be easily seen.

FIG. 3 illustrates an earplug 30 with a stiffener 32 having a wider rear end 34 than its front end 36 or middle 40. The wider rear end assures that the stiffener will receive the forward pushing force that a person applies to the rear end 42 of the body 44 during insertion into the ear canal, even if the person is careless about applying the force along the middle of the earplug rear end. The front end and middle are more likely to have to bend to follow a curved ear canal and their smaller diameters facilitate such bending. The wider, or larger diameter rear end should have a diameter H that is at least 50% greater than the front end (at a location before the curvature at the front end), with H actually being more than twice G and preferably two to four times G. G is taken rearward of a rounded end. When pushing the earplug rear end during insertion, it is desirable to turn the earplug about a quarter-turn to help insert the earplug. Such quarter turn is achieved by turning the finger that is pressing on the earplug rear end by a quarter turn. The larger diameter rear end of the stiffener makes it easier to twist the earplug.

FIG. 4 shows a method by which the earplug of FIG. 3 is formed. The body 44 of the earplug is molded in a mold cavity 50 formed between front or lower, and rear or upper mold parts 52, 54. The stiffener 32 has been previously manufactured with a small diameter (or small width if the hole is of noncircular cross-section) hole 56 in its rear end. The top mold part has a downwardly-projecting pin 60 that has a lower part 62 that lies in the stiffener hole 56. The pin has an upper part 64 that extends between the top of the stiffener and a bottom surface 66 of the upper mold part that molds the rear end of the earplug body. The stiffener is installed on the upper mold part as shown in FIG. 4, prior to the body molding process. To mold the body around the stiffener, foamable material is placed in the cavity 50 in the lower mold part (or foamable material is injected into a closed mold. Then the mold is closed, while the foamable material expands and fills the mold. A vent (not shown) allows air to escape. After the foam sets, the mold is opened and the pin 60 is pulled out of the stiffener, leaving the narrow elongated hole in the earplug. It is possible to fill the hole 26 (FIG. 3) with material, but applicant prefers to not do that.

In one example, the earplug front portion has a diameter D of 0.50 inch (12.5 mm), the pin 60 has a diameter of 0.5 mm to 4 mm, such as 1.5 mm, and the hole part 64 between the rear end of the stiffener and the rear end of the body is longer than the pin diameter, such as 6 mm long. The pin extends more than its diameter into the stiffener hole 56 to closely control the orientation of the stiffener in the mold. The pin front end that lies in the stiffener during molding can have a few ribs to more easily provide a press fit that prevents the stiffener from falling in the mold cavity and that allows easy pin withdrawal. The soft elastic foam body has a durometer of 1 to 10, shore A, while the stiffener is preferably of the soft rubber type with a durometer of at least 30 shore A.

FIG. 5 illustrates an earplug 70 that is somewhat similar to that of FIG. 4, except that the stiffener 72 is formed by a tube (with or without a slot in one side) whose passage 74 extends most or all of the way though the length of the stiffener. A pin 76 with a front end 78 extends through a long length of the stiffener. The earplug is formed in a mold 80 in a way similar to the earplug of FIG. 4. However, the stiffener passage is long and the rear end 90 of the stiffener is flush with the rear end 92 of the body (or may be recessed, or may even extend slightly rearward of the body). FIG. 6 shows that the earplug is intended to receive an end 94 of a cord 96. The cord extends between two earplugs 100, 102, with the ends 94 of the cord inserted into the tubular stiffeners in the earplugs and held therein as with adhesive, or with barbs on a stiffened cord end, or other cord attachment means such as ultrasonic welding, heat staking, etc. Such corded earplugs are used to minimize the possibility that a single earplug will fall into a vat of material being processed.

FIGS. 8 and 9 illustrate a stiffener 110 with a tapered post part 111 and with a radial (with respect to the earplug axis 112) projection 114 at its rear end. The projection 114 has recesses that form wings 115. The wings forms radially outermost locations 121–124 and gussets 126. The locations 121–124 are clamped between upper and lower parts 130, 132 of the mold 134. When foamable material is placed in the mold cavity 140, the foam material which will form the earplug body, surrounds the stiffener, except at the four location 121–124. FIG. 7 shows the final earplug, which has four small stiffener locations such as 122, 123 that can be seen.

FIG. 10 illustrates an earplug 142 similar to that of FIG. 4 but with a stiffener 143 having a wider rear end. The amount of stiffener material is minimized by forming the stiffer rear end with gussets 145 that support a wide circular rear end 146 on a post-like part 147.

FIGS. 11 and 12 illustrate an earplug 150 with a stiffener 152 formed by a plurality of rods 161–164 of material that is stiffer than the material of the soft foam body 170. Each of the rods is thin and therefore easily bent to avoid discomfort when the earplug is inserted into a curved ear canal, such as shown at 172 in FIG. 15. The four rods of FIG. 12 lie on a circle 174 centered on the earplug axis 176 and there are spaces 178 between them. The rods are each partially supported by the foam body, to resist body collapse during insertion into the ear canal. FIG. 13 shows a variation, wherein the stiffener includes two tube halves 180,182 of a tube centered on the earplug axis 184. In both FIGS. 12 and 13 the stiffeners each include a plurality of stiffeners, or stiffener portions, spaced apart along a circle that is centered on the earplug axis, with a plurality of spaces 178 or 190 between them.

FIG. 14 illustrates an earplug 200 with a stiffener 202 having a plurality of stiffener portions 211–214 that are spaced apart along a circle 216 that is centered on the earplug axis 220. The particular stiffener 202 has a center portion 222 lying at the axis and four arms 224 that connect the center portion to the stiffener portions 211–214 that lie on the circle 216. An advantage of the stiffener 202 is that the stiffener portions 211–214 and thin center portion 222 are easily bent when inserted into a curved ear canal. However, the stiffener portions 211–214 resist column collapse of the earplug body 224. The stiffeners of FIGS. 12–14 may be of constant cross-section along their entire lengths.

FIG. 16 illustrates an earplug 230 which is attached to an end of a head band 231, such as the type shown in U.S. Pat. No. 6,138,790. The earplug has a body 232, and has a stiffener 234 with a hole or passage 236. A barbed post 240 has been forced into the stiffener passage. A rear end 242 of the post is anchored in the head band. An identical earplug and post lie at the opposite end of the band.

Figure 17A:
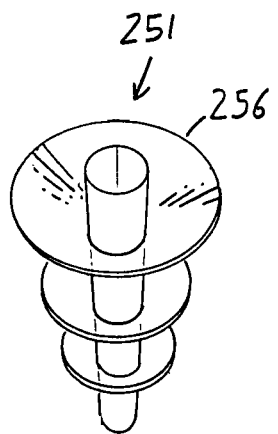
FIG. 17A is an isometric view of just the stiffener of the earplug of FIG. 17.
Figure 17:
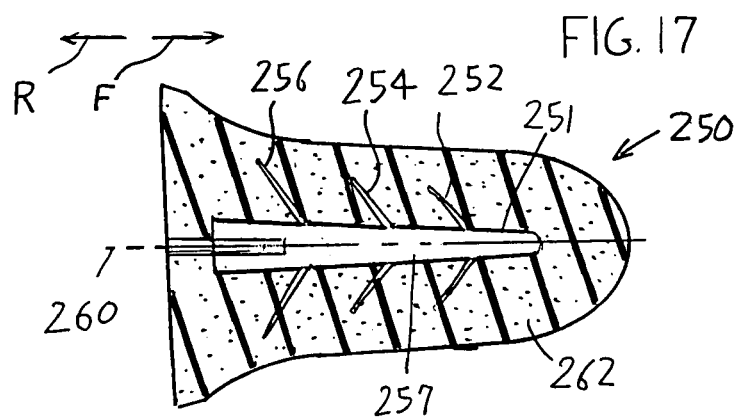
FIG. 17 is a sectional view of an earplug with a stiffener that has flanges.

FIG. 17 shows an earplug 250 with stiffener 251 having a post 257 that is tapered, and with flanges 252, 254, 256 projecting radially outwardly (with respect to axis 260) and rearward R from the post. The stiffener is encased in a soft resilient foam body 262 by being molded in the body. The flanges, which are in the shape of truncated cones that extend 360° about the axis 260, increase the blockage of noise. The stiffener is of material that is stiffer and more dense than the material of the body, and is preferably at least twice as dense. When noise encounters an interface between materials of different densities, more of the noise is blocked. The fact that the flanges extend at a radially outward-rearward incline helps in deflecting the flanges inwardly toward the axis as the earplug is installed in the ear canal. The flanges make the earplug overall more effective in blocking a range of sound frequencies. The flanges near the front end are of smaller diameters to minimize resistance to earplug compression during initial earplug insertion. The flanges add almost no resistance to bending of the earplug. In an earplug of 12.5 millimeter diameter, and therefore 6.25 mm radius (from axis 260), the flanges have a thickness of about 0.6 mm. At least one flange projects to a distance of at least 3 mm from the axis, and at least 2 mm beyond the stiffener portion that it projects from. The flanges preferably extend radially at least about half the radial distance between the outsides of the post and the outside of the body.

Figure 18:
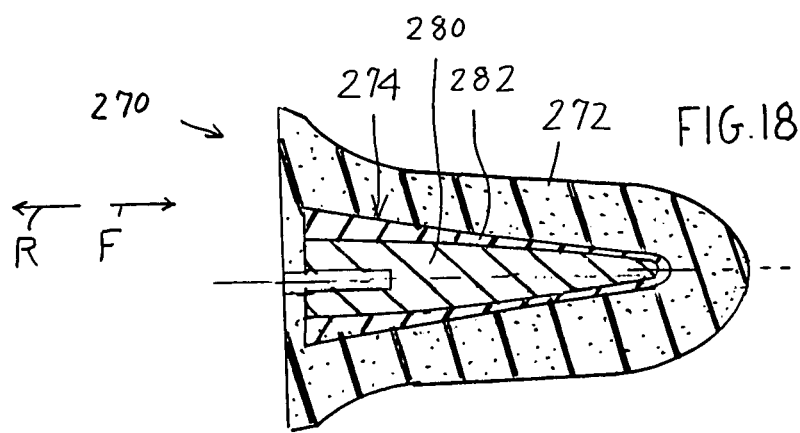
FIG. 18 is a sectional view of an earplug with a stiffener that has parts of different stiffness.

FIG. 18 shows an earplug 270 with a soft foam body 272 and with a stiffener 274. The stiffener has two portions 280–282 of materials of different stiffness but with the materials of both portions being stiffer than the material of the body 272. In one example the body is of foam having a stiffness of 2 shore A, the stiffener portion 280 has a stiffness of 10 shore A, and the stiffener portion 282 has a stiffness of 40 shore A. The stiffener is tapered in diameter, being widest at its rear end. The stiffest material such as material of stiffener portion 282 is tapered in thickness, being thickest at the rear end.

Thus the invention provides earplugs with soft resilient foam bodies (including slow recovery foam) and with elastomeric stiffeners bonded to the bodies by being molded one to the other. All of the illustrated earplugs are symmetric about their axis. An earplug with an axially aligned stiffener, is molded in a mold cavity, with the stiffener held by at least one pin that is preferably a centering pin, that extends into a hole at the rear end of the stiffener. The stiffener may or may not be concealed, especially where the stiffener is a tube that will receive an end of a cord that holds a pair of earplugs together. The stiffener may have a wide rear end, and narrow front end. A wide rear end may have locations that are clamped by parts of a mold to hold the stiffener in place. The stiffener may have a plurality of stiffener portions spaced along a circle that is concentric with the earplug axis. The stiffener may have flanges that help block noise. The stiffener may have radially inner and outer parts of different stiffness.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A method for forming an earplug with a stiffener for aiding the insertion of a front portion of the earplug into the ear canal, comprising:
   mounting the stiffener on a first mold part of a mold that has a cavity, by inserting a pin that is fixed to said first mold part, into a hole in a rear end of the stiffener;
   introducing foamable material in the mold cavity, closing the mold cavity, and allowing the foamable material to expand to fill the mold cavity and lie around the stiffener;
   removing the earplug from the cavity, including removing the pin from the stiffener.

2. The method described in claim 1 wherein:
   said first mold part has a first surface that forms a rear end of the cavity and a rear end of the earplug;
   said step of mounting the stiffener includes leaving a gap of at least one millimeter between said first surface and an extreme rear end of said stiffener, whereby to conceal the stiffener.

3. The method described in claim 2 wherein:
   said pin has a diameter of about 0.5 to 4 millimeters.

4. The method described in claim 1 wherein:
   said stiffener has a rear end;
   said step of mounting the stiffener, includes positioning the stiffener so it does not touch walls of said mold forward of the stiffener rear end except along said pin.

5. A method for forming an earplug with a soft earplug body of soft body material and with a stiffener of material that is stiffer than the material of said body, comprising:
   mounting the stiffener on a first mold part of a mold that has a cavity, by inserting a pin that is mounted on said mold part into a hole in the stiffener;
   introducing said soft body material in the mold cavity, to fill the mold cavity and lie around the stiffener;
   removing the earplug from the cavity, including removing the pin from the stiffener, and leaving a hole in at least the stiffener.

6. The method described in claim 5 wherein:
   said first mold part has a first surface that forms a rear end of the cavity and a rear end of the earplug;
   said step of mounting the stiffener includes leaving a gap of at least one millimeter between said first surface and an extreme rear end of said stiffener, whereby to conceal the stiffener.

* * * * *